(12) United States Patent
Hingston et al.

(10) Patent No.: US 9,801,749 B2
(45) Date of Patent: Oct. 31, 2017

(54) METHODS ALLOWING PYLORIC SPHINCTER TO NORMALLY FUNCTION FOR BARIATRIC STENTS

(71) Applicant: BOSTON SCIENTIFIC SCIMED, INC., Maple Grove, MN (US)

(72) Inventors: John A. Hingston, Framingham, MA (US); Claude O. Clerc, Marlborough, MA (US); Jonathan Root, Groveland, MA (US); Vishal Shah, Whitehall, PA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 5 days.

(21) Appl. No.: 14/856,953

(22) Filed: Sep. 17, 2015

(65) Prior Publication Data
US 2016/0081832 A1    Mar. 24, 2016

Related U.S. Application Data

(60) Provisional application No. 62/052,000, filed on Sep. 18, 2014.

(51) Int. Cl.
*A61F 5/00* (2006.01)
*A61F 2/844* (2013.01)
(Continued)

(52) U.S. Cl.
CPC .............. *A61F 5/0076* (2013.01); *A61F 2/04* (2013.01); *A61F 2/82* (2013.01); *A61F 2/844* (2013.01); *A61F 2/90* (2013.01); *A61F 5/0036* (2013.01); *A61F 5/0083* (2013.01); *A61F 2002/045* (2013.01); *A61F 2210/0076* (2013.01);
(Continued)

(58) Field of Classification Search
CPC ...... A61F 2250/0018; A61F 2250/0029; A61F 2250/0039; A61F 2/04; A61F 2/82; A61F 2210/0076
See application file for complete search history.

(56) References Cited

U.S. PATENT DOCUMENTS 4,501,264 A    2/1985    Rockey
4,763,653 A    8/1988    Rockey
(Continued)

FOREIGN PATENT DOCUMENTS

EP    880948 A1    12/1998
EP    2143387 A1    1/2010
(Continued)

OTHER PUBLICATIONS

International Search Report, International Application No. PCT/US2014/019119, Boston Scientific Scimed, Inc., pp. 1-6, dated May 26, 2014.

*Primary Examiner* — Leslie Deak
(74) *Attorney, Agent, or Firm* — Seager, Tufte & Wickhem, LLP

(57) ABSTRACT

A prosthesis that when implanted in the gastrointestinal tract does not impede the normal function of the pyloric sphincter. In some instances, the prosthesis is implanted as part of, or after, a sleeve gastrectomy procedure. The prosthesis includes a stent with an outer surface and a polymeric cover fully covering the outer surface of the stent. The stent includes a proximal stent flange; a proximal stent segment extending distally from the proximal stent flange; and an enlarged stent segment extending distally from the proximal stent segment.

19 Claims, 7 Drawing Sheets

(51) Int. Cl.
*A61F 2/82* (2013.01)
*A61F 2/90* (2013.01)
*A61F 2/04* (2013.01)

(52) U.S. Cl.
CPC ............... *A61F 2250/0018* (2013.01); *A61F 2250/0029* (2013.01); *A61F 2250/0039* (2013.01)

(56) References Cited

U.S. PATENT DOCUMENTS

| | | |
|---|---|---|
| 5,084,061 A | 1/1992 | Gau et al. |
| 5,238,004 A | 8/1993 | Sahatjian et al. |
| 6,302,917 B1 | 10/2001 | Dua et al. |
| 6,508,803 B1 | 1/2003 | Horikawa et al. |
| 6,527,802 B1 | 3/2003 | Mayer |
| 6,675,809 B2 | 1/2004 | Stack et al. |
| 7,025,791 B2 | 4/2006 | Levine et al. |
| 7,037,344 B2 | 5/2006 | Kagan et al. |
| 7,101,392 B2 | 9/2006 | Heath |
| 7,111,627 B2 | 9/2006 | Stack et al. |
| 7,121,283 B2 | 10/2006 | Stack et al. |
| 7,152,607 B2 | 12/2006 | Stack et al. |
| 7,267,694 B2 | 9/2007 | Levine et al. |
| 7,608,086 B2 | 10/2009 | Tanaka et al. |
| 7,608,114 B2 | 10/2009 | Levine et al. |
| 7,674,271 B2 | 3/2010 | Bjerken |
| 7,695,446 B2 | 4/2010 | Levine et al. |
| 7,758,535 B2 | 7/2010 | Levine et al. |
| 7,794,447 B2 | 9/2010 | Dann et al. |
| 7,837,669 B2 | 11/2010 | Dann et al. |
| 7,846,138 B2 | 12/2010 | Dann et al. |
| 8,282,598 B2 | 10/2012 | Belhe et al. |
| 8,702,641 B2 | 4/2014 | Belhe et al. |
| 8,702,642 B2 | 4/2014 | Belhe et al. |
| 8,870,806 B2 | 10/2014 | Levine et al. |
| 9,011,365 B2 | 4/2015 | Connor |
| 9,044,300 B2 | 6/2015 | Belhe et al. |
| 2002/0032486 A1 | 3/2002 | Lazarovitz et al. |
| 2004/0039452 A1 | 2/2004 | Bessler |
| 2004/0107004 A1 | 6/2004 | Levine et al. |
| 2005/0049718 A1 | 3/2005 | Dann et al. |
| 2005/0125075 A1 | 6/2005 | Meade et al. |
| 2005/0273060 A1 | 12/2005 | Levy et al. |
| 2006/0015190 A1 | 1/2006 | Robertson |
| 2006/0020247 A1 | 1/2006 | Kagan et al. |
| 2006/0064120 A1 | 3/2006 | Levine et al. |
| 2006/0074481 A1 | 4/2006 | Vardi et al. |
| 2007/0265709 A1 | 11/2007 | Rajan et al. |
| 2007/0282452 A1 | 12/2007 | Weitzner et al. |
| 2007/0282453 A1 | 12/2007 | Weitzner et al. |
| 2008/0033574 A1 | 2/2008 | Bessler et al. |
| 2008/0058887 A1 | 3/2008 | Griffin et al. |
| 2008/0195226 A1 | 8/2008 | Williams et al. |
| 2008/0221599 A1 | 9/2008 | Starksen |
| 2009/0012544 A1 | 1/2009 | Thompson et al. |
| 2009/0093767 A1 | 4/2009 | Kelleher |
| 2009/0192588 A1 | 7/2009 | Shin et al. |
| 2009/0248171 A1 | 10/2009 | Levine et al. |
| 2009/0287145 A1 | 11/2009 | Cragg et al. |
| 2010/0049224 A1 | 2/2010 | Vargas |
| 2010/0100105 A1 | 4/2010 | Bates et al. |
| 2010/0256775 A1 | 10/2010 | Belhe et al. |
| 2010/0298631 A1 | 11/2010 | Stack et al. |
| 2011/0087146 A1 | 4/2011 | Ryan et al. |
| 2011/0307070 A1 | 12/2011 | Clerc et al. |
| 2012/0004676 A1 | 1/2012 | Vargas |
| 2012/0065571 A1 | 3/2012 | Thompson et al. |
| 2012/0116286 A1 | 5/2012 | Williams et al. |
| 2012/0232361 A1 | 9/2012 | Birk |
| 2012/0253259 A1 | 10/2012 | Belhe et al. |
| 2014/0213960 A1 | 7/2014 | Belhe et al. |
| 2014/0243950 A1 | 8/2014 | Weiner |
| 2014/0276338 A1 | 9/2014 | Pattison et al. |
| 2015/0088048 A1 | 3/2015 | Vargas |

FOREIGN PATENT DOCUMENTS

| | | |
|---|---|---|
| FR | 2834199 A1 | 7/2003 |
| WO | 9719653 A1 | 6/1997 |
| WO | 03057079 A1 | 7/2003 |
| WO | 2007136468 A2 | 11/2007 |
| WO | 2008030403 A1 | 3/2008 |
| WO | 2009132309 A1 | 10/2009 |
| WO | 2009149294 A1 | 12/2009 |
| WO | 2011137318 A2 | 11/2011 |

METHODS ALLOWING PYLORIC SPHINCTER TO NORMALLY FUNCTION FOR BARIATRIC STENTS

CROSS-REFERENCE TO RELATED APPLICATIONS

This application claims priority to U.S. Provisional Patent Application Ser. No. 62/052,000, filed on Sep. 18, 2014, the contents of which are fully incorporated herein by reference.

BACKGROUND

Obesity is a medical condition in which excess body fat has accumulated to the extent that it may have an adverse effect on health, leading to reduced life expectancy and/or increased health problems. Body mass index (BMI), a measurement which compares weight and height, defines people as overweight (pre-obese) when their BMI is between 25 kg/m$^2$ and 30 kg/m$^2$, and obese when it is greater than 30 kg/m$^2$. Obesity is most commonly caused by a combination of excessive dietary calories, lack of physical activity, and genetic susceptibility. On average, obesity reduces life expectancy by six to seven years. Obesity increases the likelihood of various diseases, particularly heart disease, type 2 diabetes, breathing difficulties during sleep, certain types of cancer, and osteoarthritis. Obesity is a leading preventable cause of death worldwide, with increasing prevalence in adults and children, and authorities view it as one of the most serious public health problems of the 21st century. The WHO estimated in 2005 that at least 400 million adults (9.8%) worldwide were obese. According to a CDC report, 34% of adults and 17% of children in the United States were obese in 2007-2008. Obesity has been estimated to cause up to 365,000 deaths per year in the United States.

Bariatric (or weight loss) surgeries are surgical treatments for treating severe obesity (BMI greater than 40 kg/m$^2$ or BMI greater than 35 kg/m$^2$ with a comorbidity). The most common bariatric surgery is Roux-en-Y Gastric Bypass (RYGB) (FIG. 1), in which a small gastric pouch and an alimentary limb (Roux limb) are created and anastomosed to one another and to the patient's jejunum, bypassing part of the small intestine. Other bariatric surgeries, as shown in FIG. 2, may involve removal of a portion of the stomach (sleeve gastrectomy or biliopancreatic diversion with duodenal switch). In biliopancreatic diversion with duodenal switch, about 80 percent of the stomach is removed, forming a thin sleeve-like stomach. The valve (pylorus) that releases food to the small intestine remains along with a limited portion of the small intestine (duodenum) that normally connects to the stomach. The surgery bypasses the majority of the intestine by connecting the end portion of the intestine to the duodenum near the stomach (biliopancreatic diversion). This weight-loss surgery is effective but has more risks, such as malnutrition and vitamin deficiencies, and requires close monitoring. It is generally used for people who have a body mass index greater than 50 kg/m$^2$. About 150,000 patients undergo bariatric surgery each year. Long-term studies show the procedures cause significant long-term loss of weight, recovery from diabetes, improvement in cardiovascular risk factors, and a reduction in mortality of 23% to 40%.

It is reported that post-operative leaks occur in about 2% to 3% of bariatric surgery cases, but the real number may be higher due to underreporting. For RYGBP, leaks mostly occur along the stapling line of the gastric pouch and at the gastrojejunal anastomosis. However, leaks can also occur along the Z line between the esophagus and the stomach. Leaks are one of the most dreaded complications after bariatric surgery and are associated with increased morbidity and mortality. Leaks can be treated with several modalities, including site drainage with parenteral nutrition and bowel rest, various endoscopic methods (esophageal stents, clips, glue, sutures), and a second bariatric surgery. These treatment modalities all have drawbacks.

Esophageal stents have been successfully used to treat leaks after sleeve gastrectomy. These stents are prone to migration, however, because their shape is not adapted to the modified stomach geometry after sleeve gastrectomy. Two stents are often employed because existing stents are simply too short for a successful treatment.

For sleeve gastrectomy, most of the leaks occur in the upper part (the proximal third) of the sleeve. This occurs because the upper part is less accessible during surgery and more difficult to staple and also when there is a stricture in the incisura region of the stomach that creates an increase in pressure in the upper part of the sleeve. FIG. 3 is included as a representation of the stomach geometry prior to sleeve gastrectomy and FIG. 4 is included as a representation of the stomach geometry after sleeve gastrectomy.

Without limiting the scope of the disclosure a brief summary of some embodiments of the present disclosure is set forth below. Additional details of the summarized embodiments and/or additional embodiments of the present disclosure may be found in the Detailed Description below.

SUMMARY

In at least one embodiment, the present disclosure is directed to a prosthesis that is configured to allow for the pyloric sphincter to function normally when the prosthesis is implanted.

A prosthesis as disclosed herein may comprise a single stent layer and a polymeric layer. The single stent layer may comprise a stent and the polymeric layer may comprise a polymeric cover.

A method of forming the prosthesis includes forming a proximal stent comprising a proximal stent flange, a proximal stent segment, and an enlarged stent segment; forming a distal stent comprising a distal stent flange; applying a polymeric material to cover the proximal and distal stents; forming a connecting segment; and combinations thereof.

The method of forming the prosthesis may include forming a tie.

The method of forming the proximal and/or distal stent may include interweaving at least one stent filament; wherein interweaving includes, braiding, knitting, and knotting.

The stent may consist of a proximal stent flange; a proximal stent segment; an enlarged stent segment; wherein the proximal stent segment connects the proximal stent flange and the enlarged stent segment.

The stent may consist of a proximal stent flange; a proximal stent segment; an enlarged stent segment; and a short distal segment; wherein the proximal stent segment connects the proximal stent flange and the enlarged stent segment; and the short distal segment extends distally from the enlarged stent segment.

The stent may comprise a first stent and a second stent interconnected only by the polymeric cover; the first stent comprising a proximal stent flange; a proximal stent segment extending distally from the proximal stent flange; and an enlarged stent segment extending distally from the proximal stent segment; and the stent second comprising a distal stent flange.

The stent may consist of a proximal stent flange; a proximal stent segment extending distally from the proximal stent flange; an enlarged stent segment extending distally from the proximal stent segment; a connecting segment extending distally from the enlarged stent segment, and a distal stent flange extending distally from the connecting segment.

The prosthesis may comprise: a stent with an outer surface, the stent comprising: a proximal stent flange; a proximal stent segment extending distally from the proximal stent flange; an enlarged stent segment extending distally from the proximal stent segment; and a polymeric cover.

The prosthesis may comprise: a stent with an outer surface, the stent comprising: a proximal stent flange; a proximal stent segment extending distally from the proximal stent flange; an enlarged stent segment extending distally from the proximal stent segment; a polymeric cover fully covering the outer surface of the stent, the polymeric cover forming an outer surface of the prosthesis.

The prosthesis defines a lumen. The prosthesis may have a longitudinal length of about 340 mm to about 410 mm. The prosthesis may have a variable diameter.

The stent may extend from a first end of the prosthesis to a second end of the prosthesis. The stent may be laser cut or interwoven. The stent may be self-expandable. The stent may be formed by a stent filament. The stent filament may be a composite fiber.

The proximal stent flange may have a longitudinal length of about 20 mm to about 40 mm, preferably about 30 mm. The proximal stent flange may have a diameter of about 20 mm to about 30 mm, preferably about 25 mm, at its widest point. The proximal stent flange may have a first section with a uniform diameter and a second section that is tapered. The first section may form a proximal end of the proximal stent flange and the second section may form a distal end of the proximal stent flange.

The proximal stent segment may have a longitudinal length of about 100 mm to about 200 mm, preferably about 150 mm. The proximal stent segment may have a diameter of about 10 mm to about 20 mm, preferably about 20 mm. The diameter of the proximal stent segment may be uniform.

The enlarged stent segment may have a variable diameter. The enlarged stent segment may have an ovoid shape. The first end of the enlarged stent segment may have a smaller diameter than the second end. The enlarged stent segment may have a longitudinal length of about 40 mm to about 80 mm, preferably about 60 mm. The enlarged stent segment may have a diameter of about 30 mm to about 70 mm, preferably about 50 mm, at its widest point.

The proximal stent flange may form a proximal stent end and the enlarged stent segment may form a distal stent end.

The stent may include a short distal segment extending distally from the enlarged stent segment. The short distal segment may form the distal end of the stent. The short distal segment may have a longitudinal length of about 10 mm to about 30 mm, preferably about 20 mm. The short distal segment may have a diameter of about 15 mm to about 25 mm, preferably about 20 mm. The diameter of the short distal segment may be uniform.

The stent may further include a connecting segment extending distally from the enlarged stent segment. The connecting segment may have a longitudinal length of about 30 mm to about 70 mm, preferably about 50 mm. The connecting segment may have a diameter of about 15 mm to about 25 mm, preferably about 20 mm. The connecting segment may be constructed and arranged to exert no or very little radial force when the prosthesis is implanted for the normal function of the pyloric sphincter. The connecting segment may be constructed and arranged to radially increase and decrease in diameter as the pyloric sphincter opens/closes. The connecting segment may be formed by a section of the polymeric cover. The connecting segment may be a braided connecting segment.

The section of the polymeric cover may be supported by a tie. The tie may have a longitudinal length of about 30 mm to about 70 mm. The tie may be a longitudinal strut. The tie may be a stent filament. A plurality of stent filaments may be braided to form a braided strut tie. The tie may be welded to the enlarged stent segment and to the distal stent flange.

The stent may further include a distal stent flange extending distally from the connecting segment. The distal stent flange may have a longitudinal length of about 20 mm to about 40 mm, preferably 30 mm. The distal stent flange may have a diameter of about 20 mm to about 30 mm, preferably about 25 mm, at its widest point. The distal stent flange may have a first section with a uniform diameter and a second section that is tapered. The second section may form a proximal end of the proximal stent flange and the first section may form a distal end of the distal stent flange. The distal stent flange may form a distal stent end and the proximal stent flange may form a proximal stent end.

The stent filament may be braided at a first braid angle to form the proximal stent flange, the proximal stent segment, the enlarged stent segment, and the distal stent flange. The stent filament may be braided at a second braid angle to form the braided connecting segment. The second braid angle may be less than the first braid angle. The first braid angle may be about 120° and the second braid angle may be about 60°.

The stent may further include a distal stent flange. The polymeric cover may form a connecting segment engaging the enlarged stent segment to the distal stent flange.

The proximal stent flange segment may form a proximal stent end and the distal stent flange may form a distal stent end.

The stent may include a first stent comprising the proximal stent flange, the proximal stent segment, and the enlarged stent segment; a second stent comprising the distal stent flange; wherein the first and second stents are connected only by a section of the polymeric cover.

The polymeric cover may fully cover the outer surface of the stent. The polymeric cover may form the outer surface of the prosthesis. The polymeric cover may be tubular. The polymeric cover may comprise silicone. The polymeric cover may be resistant to degradation; impermeable; occlude leaks; reduce tissue in-growth; and combinations thereof. The polymeric cover is secured to the stent. The polymeric cover may comprise a first polymeric cover secured to the outer surface of the stent and a second polymeric cover secured to the inner surface of the stent. The polymeric cover may comprise a material selected from the group consisting of silicone; styrene isoprene butadiene (SIBS), expanded polytetrafluoroethylene (ePTFE), polyurethane, and combinations thereof.

The prosthesis may include a layer of therapeutic agent on an outer surface of the polymeric cover.

These and other embodiments are pointed out with particularity in the claims annexed hereto and forming a part hereof. However, for further understanding reference can be made to the drawings which form a further part hereof and the accompanying descriptive matter, in which one or more embodiments are illustrated and described.

DETAILED DESCRIPTION

Figure 2:
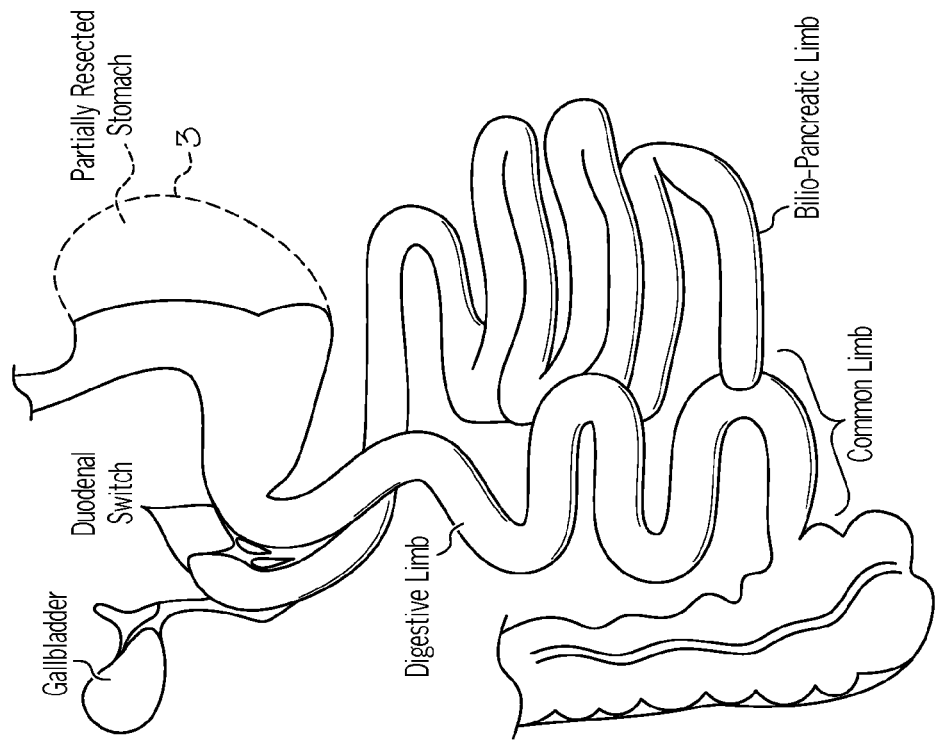
FIG. 2 is a schematic view of portions of an alimentary canal after a biliopancreatic diversion with duodenal switch procedure.
Figure 1:
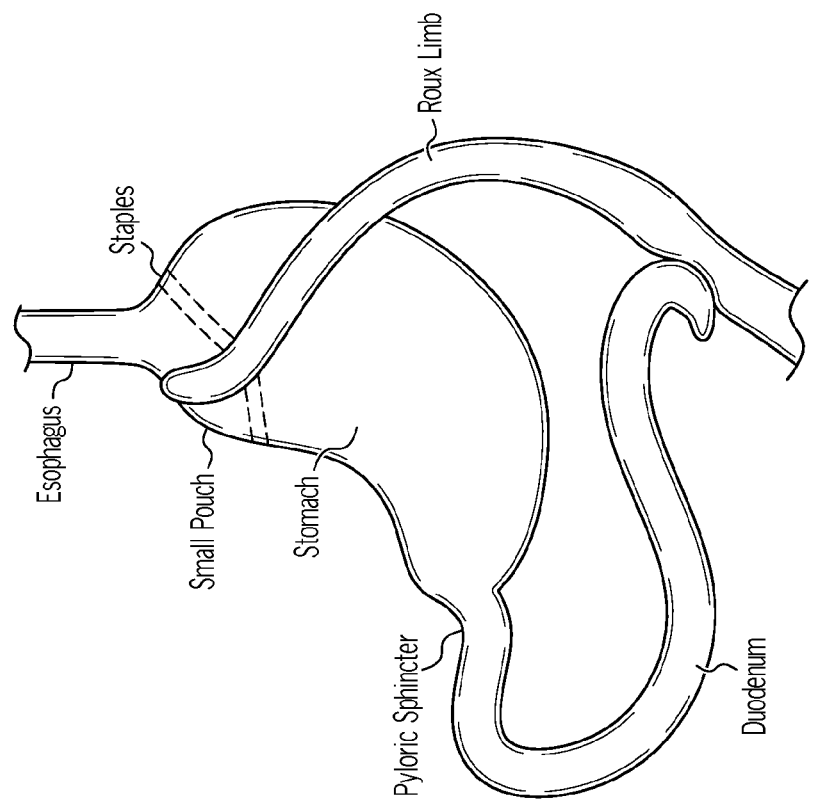
FIG. 1 is a schematic view of portions of an alimentary canal after a Roux-en-Y procedure.
Figure 4:
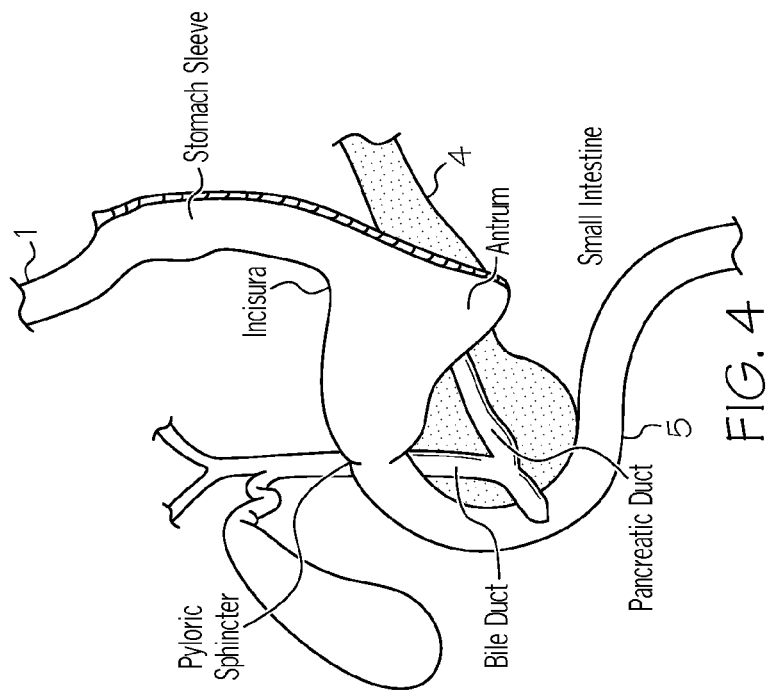
FIG. 4 is a schematic view of the modified geometry of the stomach after sleeve gastrectomy.
Figure 3:
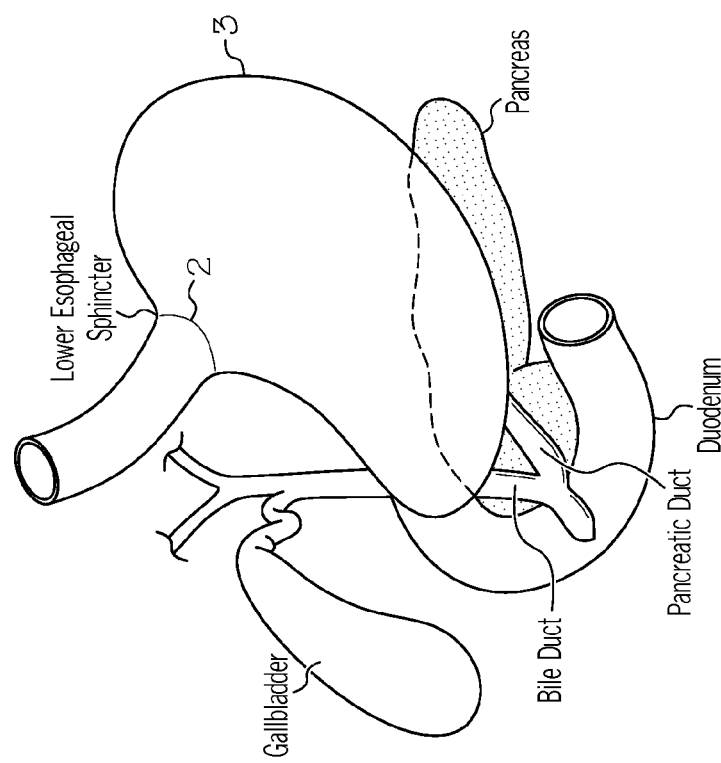
FIG. 3 is a schematic view of the geometry of the stomach prior to sleeve gastrectomy.

While the subject matter of the present disclosure may be embodied in many different forms, there are described in detail herein specific preferred embodiments of the present disclosure. This description is an exemplification of the principles of the present disclosure and is not intended to limit the present disclosure to the particular embodiments illustrated.

For the purposes of this disclosure, like reference numerals in the figures shall refer to like features unless otherwise indicated.

Definitions are provided for the following defined terms. It is intended that these definitions be applied, unless a different definition is given in the claims or elsewhere in this disclosure.

All numeric values are herein assumed to be modified by the term "about," whether or not explicitly indicated. The term "about" includes numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

The term "uniform" includes variations incurred during manufacturing.

As used in this disclosure and the appended claims, the singular forms "a", "an", and "the" include plural referents unless the content clearly dictates otherwise. As used in this disclosure and the appended claims, the term "or" is generally employed in its sense including "and/or" unless the content clearly dictates otherwise.

As used in this disclosure, the terms "connect" or "engage" do not include "indirect" connection or engagement.

The prosthesis and elements forming the prosthesis, each have a width, length, and thickness. As used in this disclosure, "thickness" is measured radially from the outer surface of the prosthesis to the inner surface of the prosthesis; "width" is measured in a circumferential direction; and "length is measured in a longitudinal direction.

As used in this disclosure, an "inner surface" of the prosthesis is a surface that defines the lumen of the prosthesis and the "outer surface" of the prosthesis is opposite the inner surface.

As used in this disclosure, a "cover" 14 extends over the openings defined by the stent wall thereby occluding the openings and preventing tissue growth through the openings and into the lumen of the prosthesis. The stent 12 may be a fully covered stent. As used herein a "fully covered stent" has a cover 14 that extends at least from the first end to the second end of the stent. Thus, the cover 14 of a fully covered stent has a length equal to or greater than the length of the stent 12. As used herein a "partially covered stent" has a cover 14 with a longitudinal length less than the longitudinal length of the stent 12.

A layer or coating of therapeutic agent as used in this disclosure is not a cover 14 as used herein.

As used in this disclosure the reference point for "proximal" and "distal" is the mouth or beginning of the gastrointestinal tract, with the "proximal" end of the prosthesis 10 configured to be positioned closer to the beginning of the gastrointestinal tract than the "distal" end of the prosthesis 10 when the prosthesis 10 is implanted in the gastrointestinal tract.

As used in this disclosure, an "end" is the last part or extremity of an element, while an "end region" is a region adjacent to, and includes, the "end."

As used in this disclosure, a "region" or "section" is a portion of the tubular prosthesis 10 that extends from a first longitudinal position to a second longitudinal position, extends around the entire circumference of the tubular prosthesis.

As used herein "diameter" is the distance of a straight line extending between two points and does not indicate a particular shape.

The following detailed description should be read with reference to the drawings in which similar elements in different drawings are numbered the same. The drawings, which are not necessarily to scale, depict illustrative embodiments and are not intended to limit the scope of the disclosure.

A. Prosthesis

The pylorus, through the pyloric sphincter, regulates entry of food from the stomach into the duodenum by opening and closing. The pyloric sphincter is a band of muscle surrounding the pyloric orifice, which marks the junction between the stomach and the duodenum. If the pyloric orifice is maintained in an open state such that the duodenum is open, bile regurgitation into the stomach and esophagus can occur. This can cause discomfort. Bile reflux is more likely to happen with a sleeve gastrectomy than in a biliopancreatic diversion with duodenal switch because in the later, the bile would have to travel through the digestive limb.

A prosthesis 10 as disclosed herein is constructed and arranged to be implanted in the gastrointestinal tract. The prosthesis is expandable from a smaller diameter delivery configuration to a larger diameter implanted configuration, as is known in the art.

A prosthesis 10 as disclosed herein is constructed and arranged to allow the pyloric sphincter to function normally when the prosthesis is implanted (see e.g. FIGS. 5A-8). As discussed below in greater detail, normal function of the pyloric sphincter may occur where the distal end of the implanted prosthesis 10 is positioned proximal to the pyloric sphincter, or where the segment of the implanted prosthesis 10 that spans the pyloric sphincter is configured so that it does not impede the normal opening and closing of the pyloric sphincter. In some instances, the prosthesis 10 is implanted as part of, or after, a sleeve gastrectomy procedure. In these instances, the prosthesis 10 can be referred to as a bariatric prosthesis.

The prosthesis 10 defines a lumen (see e.g. FIGS. 5-8). The prosthesis 10 may have no valve structure to regulate flow through the lumen of the prosthesis (see e.g. FIGS. 5-8). As discussed herein, flow through the lumen may be regulated only by the connecting segment 22.

A prosthesis 10 as disclosed herein may be self-expandable, have a longitudinal length of about 340 mm to about 410 mm, have a variable diameter, and combinations thereof. The prosthesis 10 includes a polymeric cover layer and a single stent layer (see e.g. FIGS. 5-7). The lumen of the prosthesis 10 may be defined in part by the single stent layer or by an inner polymeric cover.

A.1. POLYMERIC COVER LAYER OF PROSTHESIS

The polymeric cover layer may improve the ability of the prosthesis 10 to occlude leaks, reduce tissue in-growth, and combinations thereof. The polymeric cover layer may be resistant to degradation, may be permeable, and combinations thereof.

The polymeric cover layer includes a polymeric cover 14. The polymeric cover 14 covers some or all of the longitudinal length of the stent 12. Thus the stent 12 may be a partially covered stent or a fully covered stent. The polymeric material may be applied to the stent 12 in any suitable manner to form the polymeric cover 14, for example, but not limited to dip coating or spray coating. Alternatively, the polymeric cover 14 may be tubular and secured to the stent 12 by an interference fit, by sutures, or by any other suitable means of securement.

The prosthesis may have a single polymeric layer or two polymeric layers. The polymeric cover 14 may be a single layer forming the outer surface of the prosthesis 10 (see e.g. FIGS. 5-8), or the polymeric cover may comprise a first cover forming the outer surface of the prosthesis and a second cover forming the inner surface of the prosthesis (not shown). Where the prosthesis 10 has two polymeric layers, a first polymeric layer may cover the outer surface of the stent layer/stent 12 and a second polymeric layer may cover the inner surface of the stent layer/stent 12.

Suitable materials for the polymeric cover 14 include silicone; styrene isoprene butadiene (SIBS); expanded polytetrafluoroethylene (ePTFE); polyurethane; and combinations thereof. The polymeric cover 14 may be made of a material that swells and/or coated with an agent that swells in situ.

A.2. STENT LAYER OF PROSTHESIS

The prosthesis 10 has a single stent layer (see e.g. FIGS. 5-8). The single stent layer may be formed by a stent 12. The stent 12 may be shaped to prevent distal or proximal migration. The stent 12 forms the first and second ends of the prosthesis 10.

The stent 12 may be formed of one or more interwoven stent filaments. As used herein, interwoven includes braided stent filaments, knitted stent filaments, and knotted stent filaments. Some examples of braided stents include Wall-Flex®, Wallstent®, and Polyflex® stents made and distributed by Boston Scientific. An example of a knitted stent is the Ultraflex™ stent made by Boston Scientific, and an example of a knotted stent is the Precision Colonic™ stent made by Boston Scientific. The stent 12 may be laser cut. Alternatively, the stent 12 can be a combination of any of the above-mentioned stent types.

The stent 12 is expandable from a smaller diameter delivery configuration to a larger diameter implanted configuration, as is known in the art. The stent 12 may be self-expandable.

Suitable materials for the stent filaments include alloys such as Elgiloy® and Nitinol®; polymers such as polyethylene terephthalate (PET); biodegradable polymers; and radiopaque materials. The stent filaments may be cored or composite fibers, e.g., having a Nitinol™ outer shell and a platinum core. Some examples of cored or composite fibers are disclosed in U.S. Pat. Nos. 7,101,392, and 6,527,802, each of which are incorporated by reference in its entirety.

The stent 12 includes a proximal stent flange 20, a proximal stent segment 18, and an enlarged stent segment 16 (e.g. FIGS. 5A-8). The proximal stent segment 18 connects the proximal stent flange 20 and the enlarged stent segment 16.

Figure 8:
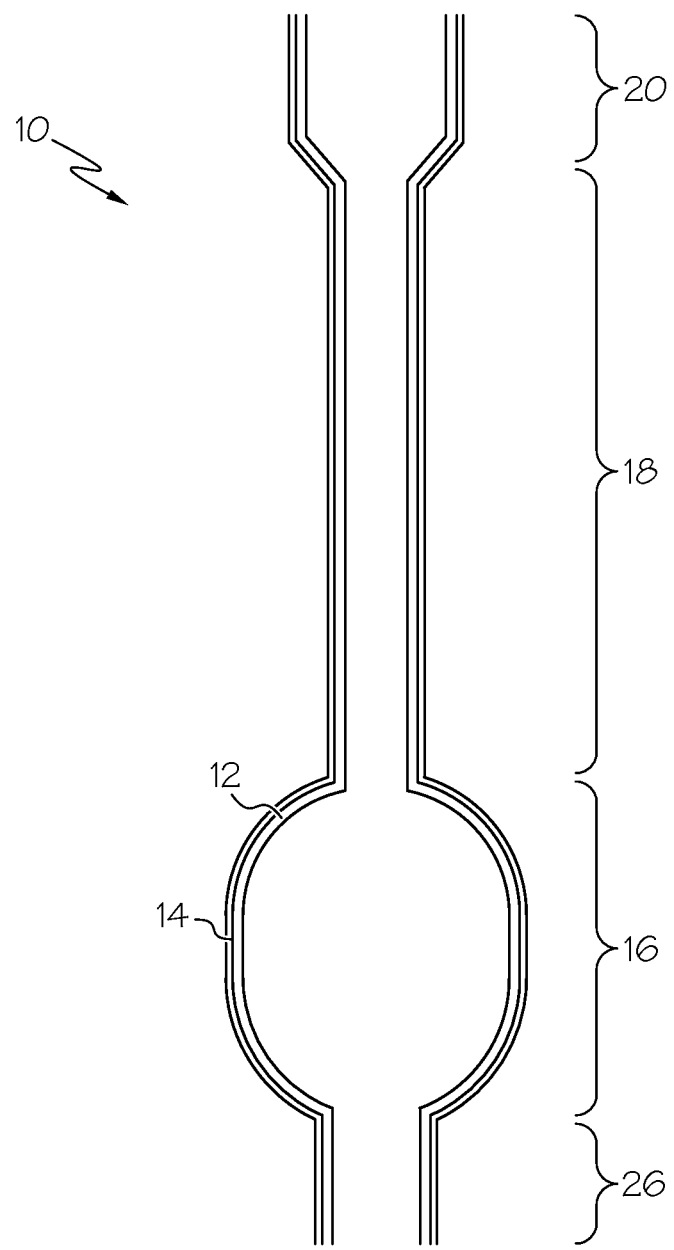
FIG. 8 is a schematic cross-sectional view of an embodiment of a prosthesis.

The stent 12 may further include a short distal segment 26 extending distally from the enlarged stent segment 16 (see e.g. FIG. 8). The short distal segment 26 may be cylindrical with a uniform diameter of about 15 mm to about 25, preferably about 20 mm and a longitudinal length of about 10 mm to about 30 mm, preferably about 20 mm. The distal end of the short distal segment 26 forms the distal end of the stent 12. When a prosthesis 10 with a short distal segment 26 is implanted, the distal end of the implanted prosthesis 10 is positioned proximal to the pyloric sphincter.

Figure 5A:
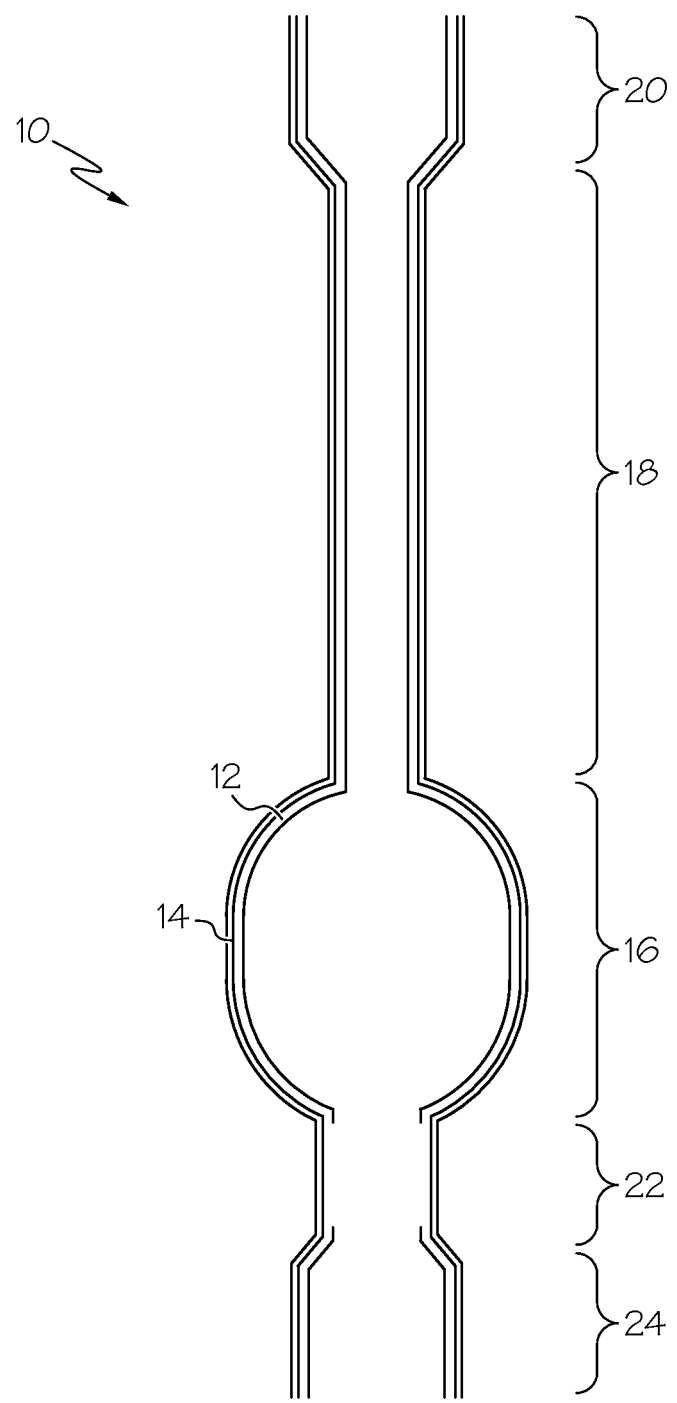
FIG. 5A is a schematic cross-sectional view of an embodiment of a prosthesis.
Figure 5B:
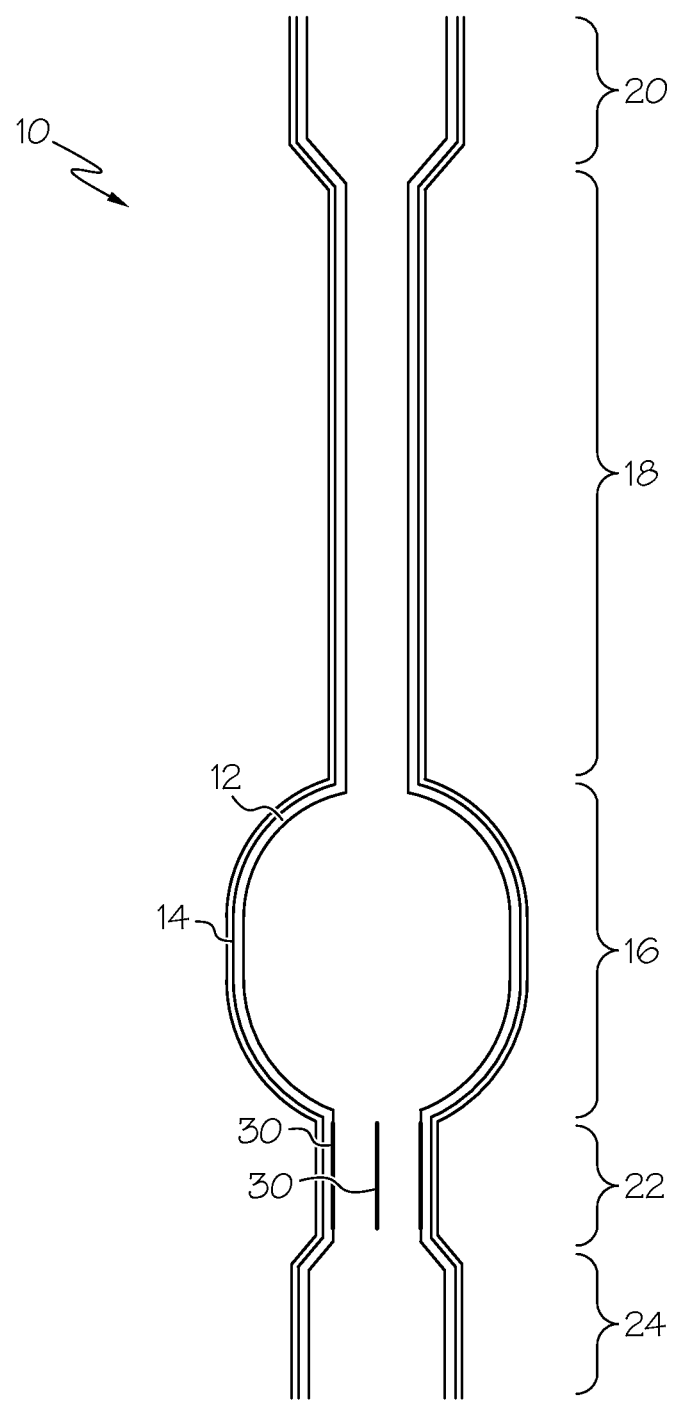
FIG. 5B is a schematic cross-sectional view of the prosthesis shown in FIG. 5A with ties.
Figure 6:
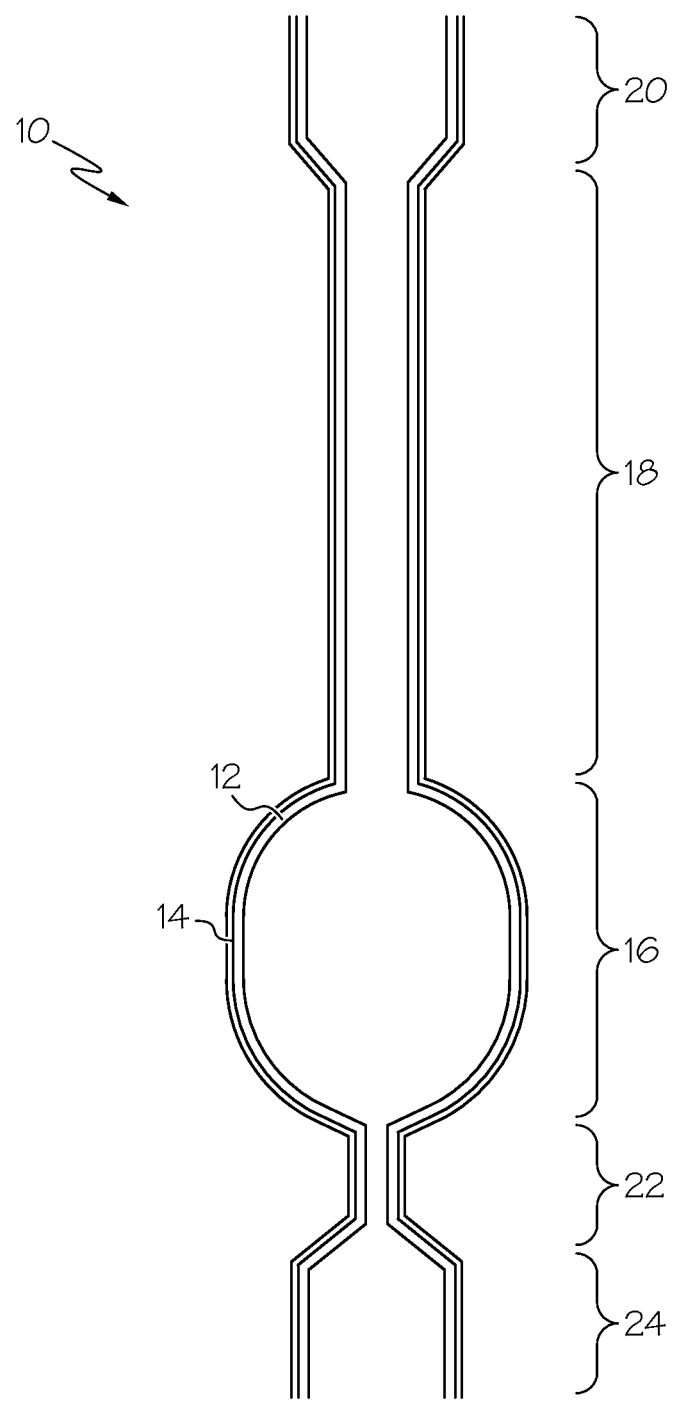
FIG. 6 is a schematic cross-sectional view of an embodiment of a prosthesis with a partially closed connecting segment.

The stent 12 may further include a distal stent flange 24 (e.g. FIGS. 5-6). The stents 12 shown in FIGS. 5A-B may be described as having a proximal stent portion comprising a proximal stent flange 20, a proximal stent segment 18, and an enlarged stent segment 16, and a distal stent portion comprising the distal stent flange 24. As discussed below in greater detail, the enlarged stent segment 16 has a diameter at its widest point that is greater than the diameter of the proximal stent segment 18 and equal to or greater than the diameter of the proximal and distal stent flanges 20, 24 at their widest points.

The prosthesis 10 may include a connecting segment 22 engaging the enlarged stent segment 16 and the distal stent flange 24 (e.g. FIGS. 5-6). As discussed below in greater detail, the connecting segment 22 may be a section of the polymeric cover 14 (supported or unsupported by a tie, e.g. FIGS. 5A-B), or a braided segment (e.g. FIG. 6).

A.2.a. Proximal Stent Flange

The proximal stent flange 20 is configured such that, when a prosthesis 10 as shown for example in FIGS. 5-8 is implanted, the proximal stent flange expands along the wall of the distal region of the esophagus to prevent any food or liquid from passing between the prosthesis and the esophageal wall.

The proximal stent flange 20 has a variable diameter. The proximal stent flange 20 flares outward such that the proximal end of the proximal stent flange 20 has a greater diameter than the distal end of the proximal stent flange 20 (see e.g. FIGS. 5-8). The proximal stent flange 20 may have a first section with a uniform diameter and a second section with a tapered diameter (see e.g. FIGS. 5-8).

The proximal stent flange 20 may be about 20 mm to about 40 mm in length, preferably about 30 mm in length, and have a diameter when expanded of about 20 mm to about 30 mm, preferably about 25 mm at its widest point. The diameter of the proximal stent flange 20 at its widest point is greater than the uniform diameter of the proximal stent segment (see e.g. FIGS. 5-8). The dimensions of the proximal stent flange 20 are provided for illustration and not limitation. It may be recognized that the dimensions of the proximal stent flange 20 can be modified to fit various anatomies.

A.2.b. Proximal Stent Segment

The proximal stent segment 18 extends distally from the proximal stent flange 20. The proximal stent segment 18 may extend distally from the tapered second section of the proximal stent flange 20 (see e.g. FIGS. 5-8). The proximal stent segment 18 is configured such that, when a prosthesis 10 as shown for example in FIGS. 5-8 is implanted, the proximal stent segment 18 extends from the distal region of the esophagus into the proximal stomach, bridging the Z line.

The proximal stent segment 18 may have a uniform diameter when expanded of about 10 mm to about 20 mm, preferably about 15 mm; have a length of about 100 mm to about 200 mm preferably about 150 mm; and combinations thereof. The dimensions of the proximal stent segment 18 are provided for illustration and not limitation. One of skill in the art will recognize that the dimensions of the proximal stent segment 18 can be modified to fit various anatomies.

A.2.c. Enlarged Stent Segment

The enlarged stent segment 16 extends distally from the proximal stent segment 18. The enlarged stent segment 16 is configured such that, when a prosthesis 10 as shown for example in FIGS. 5-8 is implanted, the enlarged stent segment 16 sits in the stomach antrum as modified by bariatric surgery. The enlarged stent segment 16 may cooperate with the proximal stent flange 20 to prevent distal or proximal migration of the prosthesis 10.

The enlarged stent segment 16 has a variable diameter when expanded (see e.g. FIGS. 5-8). The enlarged stent segment 16 may have an ovoid shape where the first end of the enlarged stent segment 16 has a smaller diameter than the second end (see e.g. FIGS. 5-8). The enlarged stent segment 16 may have a length of about 40 mm to about 80 mm, preferably about 60 mm, and a diameter when expanded of about 30 mm to about 70 mm, preferably about 50 mm at its widest point. The enlarged stent segment 16 has a diameter at its widest point that is greater than the diameter of the proximal stent flange 20 at its widest point and greater than the uniform diameter of the proximal stent segment 18 (see e.g. FIGS. 5-8). The dimensions of the enlarged stent segment 16 are provided for illustration and not limitation. One of skill in the art will recognize that the dimensions of the enlarged stent segment 16 can be modified to fit various anatomies.

A.2.d. Connecting Segment

The connecting segment 22 is constructed and arranged to span the pyloric sphincter when the prosthesis is implanted. Thus, the connecting segment 22 may be referred to as the pyloric sphincter segment of the prosthesis. The connecting segment 22 is configured such that, when a prosthesis 10 as shown for example in FIGS. 5-6 is implanted, opening and closing of the pyloric sphincter is not impeded by the prosthesis 10. For example, the connecting segment 22 may be constructed and arranged to exert little or no radial force, and/or constructed and arranged to radially increase and decrease in diameter as the pyloric sphincter opens/closes, thereby allowing the pyloric sphincter to open and close normally when the prosthesis 10 is implanted. Where the connecting segment 22 increases and decreases in diameter, flow through the lumen of the prosthesis 10 may be regulated.

The connecting segment 22 extends distally from the enlarged stent segment 16, and engages the enlarged stent segment 16 and the distal stent flange 24 (see e.g. FIGS. 5-6). Thus, the stent 12 has a proximal stent flange 20, a proximal stent segment 18, an enlarged stent segment 16, a connecting segment 22, and a distal stent flange 24.

The connecting segment 22 may be formed by a section of the polymeric cover 14 (see e.g. FIG. 5A), a tie 30 (see e.g. FIG. 5B); a braided segment (see e.g. FIG. 6); and combinations thereof. The connecting segment 22 may have a length of about 30 mm to about 70 mm, preferably about 50 mm in length and a diameter when expanded of about 15 mm to about 25 mm, preferably about 20 mm. The diameter of the connecting segment 22 may be uniform. The diameter of the connecting segment 22 may be less than the diameter of the enlarged stent segment at its widest point (see e.g. FIGS. 5-6). The dimensions of the connecting segment 22 are provided for illustration and not limitation. One of skill in the art will recognize that the dimensions of the connecting segment 22 can be modified to fit various anatomies.

Some non-limiting examples of a tie 30 include a longitudinal strut; a suture; and combinations thereof. The tie 30 may be a separate element from the stent filaments, or may be formed by one or more of the stent filaments. The number of ties should not interfere with the normal function of the pyloric sphincter when the prosthesis is implanted. The connecting segment may have one, two, three, or four ties 30. Where there are a plurality of ties 30, the ties may be circumferentially spaced apart and extend longitudinally. The tie 30 may have a length of about 30 mm to about 70 mm, preferably about 50 mm.

The polymeric cover extends over the openings defined by circumferentially adjacent ties. Thus material may not flow into/out of the prosthesis lumen through the openings defined by circumferentially adjacent ties. Thus, the prosthesis 10 is not constructed and arranged to be implanted at a bifurcation of two blood vessels.

Where the tie is a separate element from the stent filaments, the tie may be secured to the proximal and distal stents in any suitable manner. For example, the tie may be welded to the proximal and distal stents.

Where one or more stent filaments form a tie, the stent filament(s) may be braided to form a braided strut or formed into a non-braided multifilament strut. This type of tie can be referred to as an "integral tie" since it is formed by the same stent filament(s) forming the proximal stent and/or the distal stent.

Where the connecting segment 22 is a braided segment, the braided segment is formed by a stent filament braided at a very low braid angle of about 30° to 90°. A small braid angle has a low radial force and less foreshortening than a larger braid angle. For example, a 20 mm diameter connecting segment with a 60° braid angle would only elongate by 7 mm if compressed to a diameter of 6 mm. The radial pressure would be about 5 times lower than if the braid angle were 120°.

The stent filament forming the braided connecting segment 22 may also form the proximal stent flange 20, the proximal stent segment 18, the enlarged stent segment 16, and the distal stent flange 24. In this embodiment, the stent filament is braided at a braid angle of about 100° to about 140° to form the proximal stent flange 20, the proximal stent segment 18, the enlarged stent segment 16, and the distal stent flange 24.

Alternatively, where the proximal stent flange 20, the proximal stent segment 18, the enlarged stent segment 16, and the distal stent flange 24 are laser cut, a braided connecting segment 22 may be attached in any suitable manner to the enlarged stent segment 16 and to the distal stent flange 24.

A.2.e. Distal Stent Flange

The distal stent flange 24 extends distally from the connecting segment 22 (see e.g. FIGS. 5-6). The distal stent flange 24 is configured such that, when the prosthesis 10 is implanted, the distal stent flange 24 expands along the wall of the jejunum to prevent any food or liquid from passing between the prosthesis and the enteral wall.

The distal stent flange 24 flares outward such that the distal end of the distal stent flange 24 has a greater diameter than the proximal end of the distal stent flange 24 (see e.g. FIGS. 5-6). The distal stent flange 24 may have a first section with a tapered diameter and a second section with a uniform diameter (see e.g. FIGS. 5-6). The second section of the distal stent flange 24 may form a distal end of the stent 12.

The distal stent flange 24 may be about 20 mm to about 40 mm, preferably about 30 mm in length, and have a diameter when expanded of about 20 mm to about 30 mm, preferably about 25 mm at its widest point. The diameter of the distal stent flange 24 at its widest point is greater than the diameter of the connecting segment 22 (see e.g. FIGS. 5-6). The dimensions of the distal stent flange 24 are provided for illustration and not limitation. One of skill in the art will recognize that the dimensions of the distal stent flange 24 can be modified to fit various anatomies.

A.3. ADDITIONAL OPTIONAL FEATURES OF THE PROSTHESIS

The prosthesis 10 may include one or more areas, bands, coatings, members, etc. that is (are) detectable by imaging modalities such as X-Ray, MRI, ultrasound, etc. In some embodiments at least a portion of the stent is at least partially radiopaque.

The prosthesis 10 may also include one or more mechanisms for the delivery of a therapeutic agent. Often the therapeutic agent will be in the form of a coating or other layer (or layers) of material placed on a surface region of the prosthesis, which is adapted to be released at the site of the prosthesis' implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

A.4. EXAMPLES

Exemplifications of a prosthesis 10 as described above are provided in the following non-limiting examples.

Example 1

FIG. 5A shows a first example of a prosthesis 10 with a single stent layer. The prosthesis 10 has a stent 12 that is fully covered with a polymeric cover 14. The polymeric cover 14 forms the outer surface of the prosthesis 10. A prosthesis 10 as shown in FIG. 5A may be implanted after a sleeve gastrectomy procedure.

The stent 12 has a proximal stent flange 20, a proximal stent segment 18, an enlarged stent segment 16, and a distal stent flange 24. The proximal stent flange 20 defines a proximal end of the stent and the distal stent flange 24 defines a distal end of the stent 12.

The proximal and distal stent flanges 20, 24 are flared outward. The proximal end of the proximal stent flange 20 has a greater diameter than its distal end. The distal end of the distal stent flange 24 has a greater diameter than its proximal end.

The proximal stent flange 20, the proximal stent segment 18, and the enlarged stent segment 16 form a proximal stent, and the distal stent flange 24 forms a distal stent. The proximal stent has a total longitudinal length of about 240 mm, with the proximal stent flange 20 having a length of about 30 mm, the proximal stent segment 18 having a length of about 150 mm, and the enlarged stent segment 16 having a length of about 60 mm. The distal stent has a longitudinal length of about 30 mm.

The polymeric cover 14 is formed of silicone and forms the outer surface of the prosthesis 10.

The connecting segment 22 is formed by a tubular section of the polymeric cover 14. The connecting segment 22 has a longitudinal length of about 50 mm and a diameter of about 20 mm. The connecting segment 22 engages the enlarged stent segment 16 and the distal stent flange 24.

The polymeric cover 14 is formed of silicone and forms the outer surface of the prosthesis 10.

When the prosthesis 10 shown in FIG. 5A is implanted into the gastrointestinal tract, the proximal end of the prosthesis 10 is positioned in the esophagus; the distal end of the prosthesis 10 is positioned in the duodenum distal to the pyloric sphincter; the proximal end of the connecting segment 22 is positioned proximal to the pyloric sphincter; and the distal end of the connecting segment 22 is positioned in the duodenum distal to the pyloric sphincter. The connecting segment 22 is constructed and arranged to exert little or no radial force, and/or to radially increase and decrease in diameter as the pyloric sphincter opens/closes, thereby allowing the pyloric sphincter to open and close normally when the prosthesis 10 is implanted.

Example 2

FIG. 5B shows a second example of a prosthesis 10 with a single stent layer. The prosthesis 10 has a stent 12 that is fully covered with a polymeric cover 14. The polymeric cover 14 forms the outer surface of the prosthesis 10. A prosthesis 10 as shown in FIG. 5B may be implanted after a sleeve gastrectomy procedure.

The stent 12 has a proximal stent flange 20, a proximal stent segment 18, an enlarged stent segment 16, and a distal stent flange 24. The proximal stent flange 20 defines a proximal end of the stent and the distal stent flange 24 defines a distal end of the stent 12.

The proximal and distal stent flanges 20, 24 are flared outward. The proximal end of the proximal stent flange 20 has a greater diameter than its distal end. The distal end of the distal stent flange 24 has a greater diameter than its proximal end.

The proximal stent flange 20, the proximal stent segment 18, and the enlarged stent segment 16 form a proximal stent, and the distal stent flange 24 forms a distal stent. The proximal stent has a total longitudinal length of about 240 mm, with the proximal stent flange 20 having a length of about 30 mm, the proximal stent segment 18 having a length of about 150 mm, and the enlarged stent segment 16 having a length of about 60 mm. The distal stent has a longitudinal length of about 30 mm.

The polymeric cover 14 is formed of silicone and forms the outer surface of the prosthesis 10.

The connecting segment 22 has a longitudinal length of about 50 mm and a diameter of about 20 mm. The connecting segment 22 joins the enlarged stent segment 16 and the distal stent flange 24. The connecting segment 22 comprises a tubular section of the polymeric cover 14 and a tie 30. As discussed above, the tie 30 may be either a separate element or formed of a stent filament; either a non-braided strut or a braided strut; and combinations thereof.

The polymeric cover 14 is formed of silicone and forms the outer surface of the prosthesis 10.

When the prosthesis 10 shown in FIG. 5B is implanted into the gastrointestinal tract, the proximal end of the prosthesis 10 is positioned in the esophagus; the distal end of the prosthesis 10 is positioned in the duodenum distal to the pyloric sphincter; the proximal end of the connecting segment 22 is positioned proximal to the pyloric sphincter; and the distal end of the connecting segment 22 is positioned in the duodenum distal to the pyloric sphincter. The connecting segment 22 with or without a tie 30 is constructed and arranged to exert little or no radial force, and/or to radially increase and decrease in diameter as the pyloric sphincter opens/closes, thereby allowing the pyloric sphincter to open and close normally when the prosthesis 10 is implanted.

Example 3

A third example of a prosthesis 10 with a single stent layer is shown in FIG. 6. The prosthesis 10 has a stent 12 and a polymeric cover 14. The polymeric cover 14 forms the outer surface of the prosthesis 10. A prosthesis 10 as shown in FIG. 6 may be implanted after a sleeve gastrectomy procedure.

The stent 12 has a proximal stent flange 20, a proximal stent segment 18, an enlarged stent segment 16, a braided connecting segment 22, and a distal stent flange 24. FIG. 6 shows the braided connecting segment 22 in a partially closed/contracted state.

The proximal and distal stent flanges 20, 24 are flared outward. The proximal end of the proximal stent flange 20 has a greater diameter than its distal end. The distal end of the distal stent flange 24 has a greater diameter than its proximal end.

The stent 12 has a total longitudinal length of about 310 mm, with the proximal stent flange 20 having a length of about 30 mm and a diameter of about 30 mm at its widest point; the proximal stent segment 18 having a length of about 150 mm and a uniform diameter of about 15 mm; the enlarged stent segment 16 having a length of about 60 mm and a diameter of about 50 mm at its widest point; the braided connecting segment 22 having a contracted implanted length of about 57 mm, a contracted implanted diameter of about 6 mm, an expanded implanted length of about 50 mm, and an expanded implanted diameter of about 20 mm; and the distal stent flange 24 having a length of about 20 mm and a diameter of 20 mm at its widest point. The braid angle of the stent filaments forming the braided connecting segment 22 is about 60°; while the braid angle of the stent filaments forming the proximal stent flange 20, the proximal stent segment 18, the enlarged stent segment 16, and the distal stent flange 24 is about 120°.

The polymeric cover 14 is formed of silicone and forms the outer surface of the prosthesis 10.

When the prosthesis 10 shown in FIG. 6 is implanted into the gastrointestinal tract, the proximal end of the prosthesis 10 is positioned in the esophagus, the distal end of the prosthesis 10 is positioned in the duodenum distal to the pyloric sphincter; the proximal end of the braided connecting segment 22 is positioned proximal to the pyloric sphincter; and the distal end of the braided connecting segment 22 is positioned in the duodenum distal to the pyloric sphincter. The braided connecting segment 22 is constructed and arranged to exert little or no radial force, and/or to radially increase and decrease in diameter as the pyloric sphincter opens/closes, thereby allowing the pyloric sphincter to open and close normally when the prosthesis 10 is implanted.

Example 4

Figure 7:
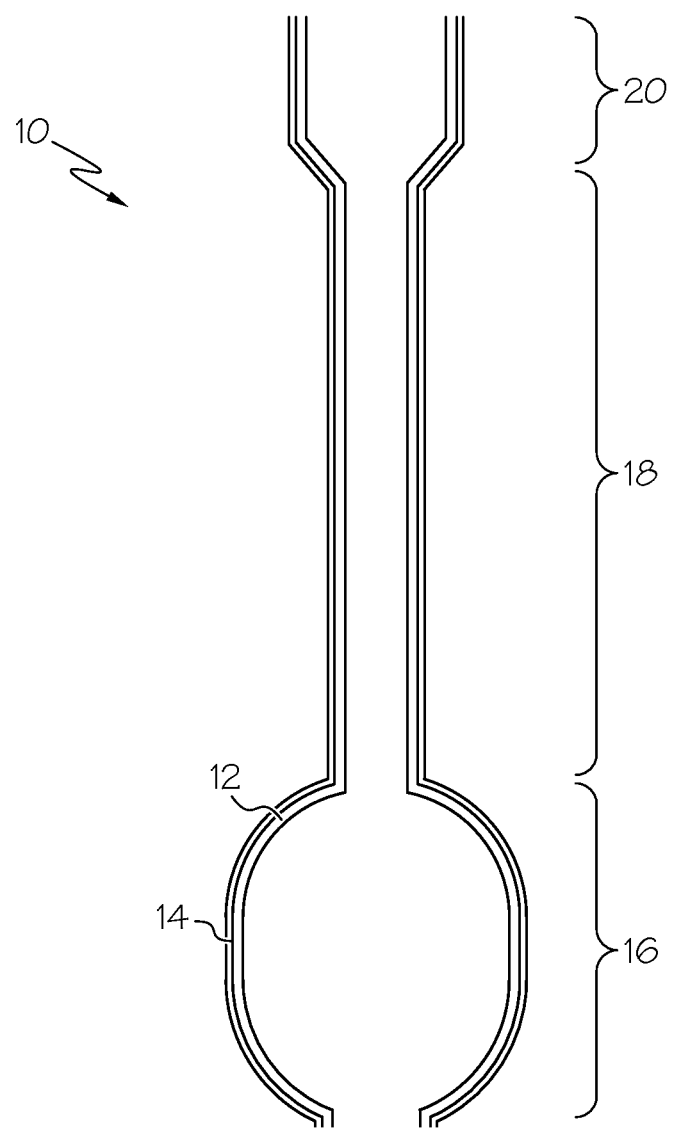
FIG. 7 is a schematic cross-sectional view of an embodiment of a prosthesis.

A fourth example of a prosthesis 10 with a single stent layer is shown in FIG. 7. The prosthesis has a stent 12 and a polymeric cover 14. The polymeric cover 14 forms the outer surface of the prosthesis 10. A prosthesis 10 as shown in FIG. 7 may be implanted after a sleeve gastrectomy procedure. The prosthesis 10 has a longitudinal length of about 240 mm.

The stent 12 has a proximal stent flange 20, a proximal stent segment 18, and an enlarged stent segment 16. The proximal stent flange 20 is flared outward with the proximal end of the proximal stent flange 20 having a greater diameter than its distal end. The stent 12 has a total longitudinal length of about 240 mm, with the proximal stent flange 20 having a length of about 30 mm and a diameter of about 30 mm at its widest point; the proximal stent segment 18 having a length of about 150 mm and is cylindrical with a uniform diameter of about 15 mm; and the enlarged stent segment 16 having a length of about 60 mm and a diameter of about 50 mm at its widest point.

The polymeric cover 14 is formed of silicone and forms the outer surface of the prosthesis 10.

The stent 12 shown in FIG. 7 may further include a short distal segment 26 extending distally from the enlarged stent segment 16 (see e.g. FIG. 8). The short distal segment 26 may be tubular with a uniform diameter equal to the uniform diameter of the proximal stent segment 18 (see e.g. FIG. 8).

When the prosthesis 10 shown in FIG. 7 is implanted in the gastrointestinal tract, the proximal end of the prosthesis 10 is positioned in the esophagus, and the distal end of the prosthesis 10 is positioned in the stomach proximal to the pyloric sphincter. Thus, the pyloric sphincter is able to function normally when the prosthesis 10 is implanted.

B. Methods of Manufacture

A method of forming a prosthesis 10 comprising a stent 12 and a polymeric cover 14, as shown in FIGS. 5A-B, includes one or more of the following steps: forming a proximal stent comprising a proximal stent flange 20, a proximal stent segment 18, and an enlarged stent segment 16; forming a distal stent comprising a distal stent flange 24; applying a polymeric material to cover the proximal and distal stents and to form a connecting segment 22; forming a tie; wherein forming the proximal and/or distal stent includes interweaving a stent filament; wherein interweaving includes, braiding, knitting, and knotting; wherein the proximal end of the proximal stent flange 20 has a greater diameter than the distal end; wherein the proximal stent segment 18 has a uniform diameter; wherein the enlarged stent segment has an ovoid shape; wherein the proximal end of the distal stent flange 24 has a smaller diameter than the distal end of the distal stent flange 24; wherein the tie is formed by the stent filament; wherein the stent filament is a plurality of stent filaments; wherein a plurality of stent filaments are braided to form a braided strut tie; wherein the tie is a separate element and secured to the proximal and distal stents; and combinations thereof.

The proximal and distal stents may be fabricated on two different braiding mandrels and then placed onto a coating mandrel for the application of the polymeric material onto the stent 12 to form the prosthesis 10 and the connecting segment 22. Alternatively, the proximal and distal stents may be fabricated on a mandrel that is also used for the application of the polymeric material onto the stent 12 to form the prosthesis 10 and the connecting segment 22. Any suitable mandrel or braiding mandrel may be used.

Where a tie 30 is formed from a stent filament, the braiding mandrel may have a section with a longitudinal groove for placing the stent filament to form the tie. Thus, for example, the braiding mandrel may have a first mandrel section for forming the proximal stent; a second mandrel section with longitudinally oriented tie grooves extending into the outer mandrel surface; and a third mandrel section for forming the distal stent. Thus, the first mandrel section is constructed and arranged to form the proximal stent flange 20, the proximal stent segment 18, and the enlarged stent segment 16; the second mandrel section is constructed and arranged to form the connecting segment 22; and the third mandrel section is constructed and arranged to form the distal stent flange 24.

A method of forming a prosthesis 10 comprising a stent 12 and a polymeric cover 14, as shown in FIG. 6, includes one or more of the following steps: forming a stent comprising a proximal stent flange 20, a proximal stent segment 18, an enlarged stent segment 16; a braided connecting segment 22; and a distal stent flange 24; applying a polymer to cover the stent 12; wherein forming the proximal and/or distal stent includes interweaving a stent filament; wherein interweaving includes, braiding, knitting, and knotting; wherein the proximal end of the proximal stent flange 20 has a greater diameter than the distal end; wherein the proximal stent segment 18 has a uniform diameter; wherein the connecting segment 22 is cylindrical; wherein the stent filament is braided and the braid angle for the stent filament forming the connecting segment 22 is less than the braid angle for the stent filament forming the other segments 16, 18, 20, 24 of the stent 12; wherein the stent filament is braided and the braid angle for the stent filament forming the connecting segment 22 is about 60°; wherein the stent filament is braided and the braid angle for the stent filament forming the other segments 16, 18, 20, 24 of the stent 12 is about 120°; wherein the proximal end of the distal stent flange 24 has a smaller diameter than the distal end of the distal stent flange 24; and combinations thereof.

A braiding mandrel for braiding a stent as shown in FIG. 6 may have a first mandrel section for braiding the stent filament at a first angle; a second mandrel section for braiding the stent filament at a second angle less than the first angle; and a third mandrel section for braiding the stent filament at the first angle; wherein the first angle is about 100° to about 140° and the second angle is about 30° to about 90°; where the first mandrel section is constructed and arranged to form the proximal stent flange 20, the proximal stent segment 18, and the enlarged stent segment 16; wherein the second mandrel section is constructed and arranged to form the braided connecting segment 22; wherein the third mandrel section is constructed and arranged to form the distal stent flange 24; and combinations thereof.

A method of forming a prosthesis 10 comprising a stent 12 and a polymeric cover 14, as shown in FIG. 7, includes one or more of the following steps: forming a stent 12 comprising a proximal stent flange 20, a proximal stent segment 18; and an enlarged stent segment 16; applying a polymer to cover the stent 12; wherein forming the proximal and/or distal stent includes interweaving a stent filament; wherein interweaving includes, braiding, knitting, and knotting; wherein the proximal end of the proximal stent flange 20 has a greater diameter than the distal end; wherein the proximal stent segment 18 is cylindrical; and combinations thereof. Examples of mandrels that may be used to braid a stent as shown in FIG. 7 are disclosed in commonly assigned U.S. 2011/0307070, incorporated by reference in its entirety.

C. Methods of Use

A prosthesis 10 as described herein may be used to treat leaks after bariatric surgery, the method comprising one or more of the following steps: deploying a prosthesis, wherein a proximal end of the prosthesis is positioned in the esophagus and a distal end of the prosthesis is positioned either proximal to the pyloric sphincter or distal to the pyloric sphincter; wherein the prosthesis is constructed and arranged to exert little or no radial force, and/or to radially increase and decrease in diameter as the pyloric sphincter opens/closes, thereby allowing the pyloric sphincter to open and close normally when the prosthesis 10 is implanted; wherein the prosthesis comprises a stent 12 and a polymeric cover 14, the polymeric cover 14 forming an outer surface of the prosthesis; wherein the stent 12 comprises a proximal stent flange 20, a proximal stent segment 18, and an enlarged stent segment 16, the enlarged stent segment defining a distal end of the prosthesis; wherein the stent 12 is a braided stent comprising a proximal stent flange 20, a proximal stent segment 18, an enlarged stent segment 16, a braided connecting segment 22, and a distal stent flange 24, the stent filament braided at a first angle to form the braided connecting segment 22; wherein the stent filament is braided at a second braid angle to form the proximal stent flange 20, the proximal stent segment 18, the enlarged stent segment 16, and the distal stent flange 24 braided, the second braid angle greater than the first braid angle; wherein the first braid angle is about 100° to about 140°, and the second braid angle is about 30° to about 90°; wherein the stent 12 forms an inner layer of the prosthesis 10 and the polymeric cover 14 forms an outer layer of the prosthesis 10; and combinations thereof.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

The invention claimed is:

1. A prosthesis comprising:
a stent with an outer surface, the stent comprising:
a proximal stent flange;
a proximal stent segment extending distally from the proximal stent flange;
an enlarged stent segment extending distally from the proximal stent segment;
a polymeric cover fully covering the outer surface of the stent, the polymeric cover forming an outer surface of the prosthesis; and
a connecting segment formed by a tubular section of the polymeric cover extending distally from the enlarged stent segment, the connecting segment consisting of the polymeric cover.

2. The prosthesis of claim 1, the stent further comprising:
a distal stent flange extending distally from the connecting segment, the distal stent flange forming a distal stent end and the proximal stent flange forming a proximal stent end;
wherein the stent comprises stent filaments, the stent filaments being braided at a first braid angle to form the proximal stent flange, the proximal stent segment, the enlarged stent segment, and the distal stent flange.

3. The prosthesis of claim 2, wherein the first braid angle is about 120°.

4. The prosthesis of claim 2, wherein the distal stent flange has a longitudinal length of about 20 mm to about 40 mm, and a diameter of about 20 mm to about 30 mm at its widest point.

5. The prosthesis of claim 1, wherein the connecting segment has a longitudinal length of about 30 mm to about 70 mm, and a diameter of about 15 mm to about 25 mm.

6. The prosthesis of claim 1, the stent further comprising a distal stent flange segment, the polymeric cover forming the tubular connecting segment engaging the enlarged stent segment to the distal stent flange, the proximal stent flange forming a proximal stent end and the distal stent flange forming a distal stent end.

7. The prosthesis of claim 1, wherein:
the proximal stent flange has a longitudinal length of about 20 mm to about 40 mm, and a diameter of about 20 mm to about 30 mm at its widest point;
the proximal stent segment has a longitudinal length of about 100 mm to about 200 mm; a uniform diameter of about 10 mm to about 20 mm; and
the enlarged stent segment has a longitudinal length of about 40 mm to about 80 mm, and a diameter of about 30 mm to about 70 mm at its widest point.

8. The prosthesis of claim 7, wherein the connecting segment has a longitudinal length of about 30 mm to about 70 mm, and a diameter of about 15 mm to about 25 mm.

9. The prosthesis of claim 1, wherein the connecting segment is constructed and arranged to exert no or very little radial force when the prosthesis is implanted for normal functioning of a pyloric sphincter.

10. The prosthesis of claim 1, wherein the polymeric cover is a silicone cover.

11. The prosthesis of claim 1, wherein the prosthesis has a single stent layer formed by the stent.

12. The prosthesis of claim 1, further comprising a distal stent flange extending distally from the connecting segment, the distal stent flange forming a distal stent end and the proximal stent flange forming a proximal stent end.

13. The prosthesis of claim 12, wherein the connecting segment is constructed and arranged to exert no or very little radial force when the prosthesis is implanted for normal functioning of a pyloric sphincter.

14. The prosthesis of claim 13, wherein:
the proximal stent flange has a longitudinal length of about 20 mm to about 40 mm, and a diameter of about 20 mm to about 30 mm at its widest point;
the proximal stent segment has a longitudinal length of about 100 mm to about 200 mm; a uniform diameter of about 10 mm to about 20 mm;
the enlarged stent segment has a longitudinal length of about 40 mm to about 80 mm, and a diameter of about 30 mm to about 70 mm at its widest point;
the connecting segment has a longitudinal length of about 30 mm to about 70 mm, and a diameter of about 15 mm to about 25 mm; and
the distal stent flange has a longitudinal length of about 20 mm to about 40 mm, and a diameter of about 20 mm to about 30 mm at its widest point.

15. A proximal bariatric prosthesis comprising a single stent layer forming an inner layer of the bariatric prosthesis and a polymeric cover forming an outer layer of the bariatric prosthesis,
the single stent layer comprising:
a proximal stent flange, the proximal stent flange forming a proximal end of the bariatric prosthesis;
a distal stent flange, the distal stent flange forming a distal end of the bariatric prosthesis;
a proximal cylindrical stent segment extending distally from the proximal stent flange;
an enlarged stent segment extending distally from the proximal cylindrical stent segment; and
a connecting segment extending distally from the enlarged stent segment to the distal stent flange, the connecting segment consisting of the polymeric cover;
wherein the polymeric cover is attached to an outer surface of the single stent layer.

16. The bariatric prosthesis of claim 15, wherein
the proximal stent flange has a longitudinal length of about 20 mm to about 40 mm, and a diameter of about 20 mm to about 30 mm at its widest point;
the proximal stent segment has a longitudinal length of about 100 mm to about 200 mm; a uniform diameter of about 10 mm to about 20 mm;
the enlarged stent segment has a longitudinal length of about 40 mm to about 80 mm, and a diameter of about 30 mm to about 70 mm at its widest point;
the connecting segment has a longitudinal length of about 30 mm to about 70 mm, and a diameter of about 15 mm to about 25 mm; and
the distal stent flange has a longitudinal length of about 20 mm to about 40 mm, and a diameter of about 20 mm to about 30 mm at its widest point.

17. The bariatric prosthesis of claim 15, wherein the connecting segment is constructed and arranged to exert no or very little radial force when the bariatric prosthesis is implanted for normal functioning of a pyloric sphincter.

18. A bariatric prosthesis comprising a single stent layer and a polymeric cover,
the single stent layer comprising:
a proximal stent, the proximal stent consisting of:
a proximal stent flange having a variable diameter;
a proximal cylindrical stent segment extending distally from the proximal stent flange, the proximal cylindrical stent segment having a uniform diameter; and an enlarged stent segment extending distally from the proximal cylindrical stent segment, the enlarged stent segment having a variable diameter; and a distal stent consisting of a distal stent flange having a variable diameter, a proximal end of the distal stent spaced apart from a distal end of the proximal stent to define a gap therebetween;

wherein the polymeric cover is attached to an outer surface of the proximal stent; is attached to an outer surface of the distal stent; and interconnects the proximal and distal stents and spans the gap between the proximal end of the distal stent and the distal end of the proximal stent.

19. The bariatric prosthesis of claim 18, wherein the proximal and distal stents are interconnected only by the polymeric cover.

\* \* \* \* \*